US010143675B2

(12) United States Patent
St. Laurent et al.

(10) Patent No.: US 10,143,675 B2
(45) Date of Patent: Dec. 4, 2018

(54) PHARMACEUTICAL COMPOSITION FOR TREATING INFLAMMATION AND PAIN

(71) Applicant: OLATEC THERAPEUTICS LLC, New York, NY (US)

(72) Inventors: Joseph P. St. Laurent, Lakeville, MA (US); Gerald S. Jones, Norwood, MA (US); David M. Bresse, Middleboro, MA (US)

(73) Assignee: OLATEC THERAPEUTICS LLC, New York, NY (US)

( * ) Notice: Subject to any disclaimer, the term of this patent is extended or adjusted under 35 U.S.C. 154(b) by 49 days.

(21) Appl. No.: 15/299,688

(22) Filed: Oct. 21, 2016

(65) Prior Publication Data

US 2017/0100364 A1 Apr. 13, 2017

Related U.S. Application Data

(60) Division of application No. 14/832,681, filed on Aug. 21, 2015, now Pat. No. 9,474,734, which is a division of application No. 14/562,620, filed on Dec. 5, 2014, now Pat. No. 9,114,122, which is a continuation of application No. PCT/US2013/045033, filed on Jun. 10, 2013.

(60) Provisional application No. 61/659,771, filed on Jun. 14, 2012.

(51) Int. Cl.
| | |
|---|---|
| *A61K 31/275* | (2006.01) |
| *A61K 47/10* | (2017.01) |
| *A61K 9/00* | (2006.01) |
| *A61K 47/20* | (2006.01) |
| *A61K 47/34* | (2017.01) |
| *A61K 9/06* | (2006.01) |

(52) U.S. Cl.
CPC ............ *A61K 31/275* (2013.01); *A61K 9/006* (2013.01); *A61K 9/0014* (2013.01); *A61K 9/0053* (2013.01); *A61K 9/06* (2013.01); *A61K 47/10* (2013.01); *A61K 47/20* (2013.01); *A61K 47/34* (2013.01)

(58) Field of Classification Search
CPC ........ A61K 47/10; A61K 47/34; A61K 47/20; A61K 31/275; A61K 9/006; A61K 9/0014
See application file for complete search history.

(56) References Cited

U.S. PATENT DOCUMENTS

| | | | |
|---|---|---|---|
| 4,424,167 A | 1/1984 | Oeckl | |
| 4,476,137 A | 10/1984 | Haviv et al. | |
| 5,053,429 A | 10/1991 | Hirsch et al. | |
| 5,175,192 A | 12/1992 | Ulrich et al. | |
| 5,348,838 A | 9/1994 | Ushirogouchi et al. | |
| 6,551,615 B1 | 4/2003 | Iyer et al. | |
| 8,476,316 B2 | 7/2013 | St. Laurent | |
| 9,114,122 B2 * | 8/2015 | St. Laurent | A61K 47/10 |
| 9,474,734 B2 * | 10/2016 | St. Laurent | A61K 47/10 |
| 2001/0025111 A1 | 9/2001 | Hansen et al. | |
| 2006/0069160 A1 | 3/2006 | Torrence | |
| 2007/0293457 A1 | 12/2007 | Baker et al. | |
| 2009/0291917 A1 | 11/2009 | Akama et al. | |
| 2010/0221336 A1 | 9/2010 | Fink et al. | |
| 2010/0240756 A1 | 9/2010 | St. Laurent | |
| 2012/0157524 A1 | 6/2012 | St. Laurent | |

OTHER PUBLICATIONS

Lee, J. et al., "Methionine analogues as inhibitors of methionyl-tRNA synthetase", Bioorganic & Medicinal Chemistry Letters, 1998, vol. 8, pp. 3511-3514.
Plewig, G. et al., "Anti-inflammatory effects of antimicrobial agents: an in vivo study", Journal of Investigative Dermatology, 1975, vol. 65, No. 6, pp. 532-536.
Juliana, C. et al., "Anti-inflammatory compounds parthenolide and Bay 11-7082 are direct inhibitors of the inflammasome", The Journal of Biological Chemistry, 2010, vol. 285, No. 13, pp. 9792-9802.
Moon, J-K., et al., "Analysis and Anti-Helicobacter Activity of Sulforaphane and Related Compounds Present in Broccoli", J. Agric. Food chem. 2010, 58, 6672-6677.
Supplementary European Search Report for European Application No. EP13804724, dated Oct. 30, 2015.
International Search Report for International Application No. PCT/US2013/045033, dated Sep. 24, 2013.

\* cited by examiner

*Primary Examiner* — Jennifer M Kim
(74) *Attorney, Agent, or Firm* — Perkins Coie LLP; Viola T. Kung

(57) ABSTRACT

The present invention is directed to a pharmaceutical composition comprising a pharmaceutically acceptable carrier and 3-(methylthio)propionitrile, or a pharmaceutically acceptable salt thereof. The present invention is directed to a method for treating inflammation, inflammatory-related disorders, or pain, by administering ω-(methylthio)alkylnitriles such as 3-(methylthio)propionitrile, or a pharmaceutically acceptable salt or solvate thereof to a subject in need thereof.

7 Claims, No Drawings

PHARMACEUTICAL COMPOSITION FOR TREATING INFLAMMATION AND PAIN

This application is a divisional of U.S. application Ser. No. 14/832,681, filed Aug. 21, 2015; which is a divisional of U.S. application Ser. No. 14/562,620, filed Dec. 5, 2014, now U.S. Pat. No. 9,114,122; which is a continuation of PCT/US2013/045033, filed Jun. 10, 2013; which claims the benefit of U.S. Provisional Application No. 61/659,771, filed Jun. 14, 2012. The contents of the above-identified applications are incorporated herein by reference in their entireties.

FIELD OF THE INVENTION

The present invention relates to a pharmaceutical composition comprising a pharmaceutically acceptable carrier and an active compound of ω-(methylation)alkyl nitrile, or its pharmaceutically acceptable salts. The present invention also relates to methods of using the compound for treating inflammation or inflammatory-related disorders and pain.

BACKGROUND OF THE INVENTION

Inflammation is a process by which microbes or tissue injury induce the release of cytokines and chemokines from various cell types producing increased blood vessel permeability, up regulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, such as mediators and antigens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Based on the physical causes, pain can be divided into three types: nociceptive, neuropathic, and mix-type.

Nociceptive pain is the term for pain that is detected by specialized sensory nerves called nociceptors. These nerves are located throughout the soft tissues, such as muscles and skin, as well as the internal organs. There are two types of nociceptive pain: somatic pain and visceral pain. Visceral pain comes from the internal organs. Deep somatic pain is initiated by stimulation of nociceptors in ligaments, tendons, bones, blood vessels, fasciac and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns. Nociceptive pain is usually short in duration and end when the damage recovers. Examples of nociceptive pain include postoperative pain, sprains, bone fractures, burns, bumps, bruises, and inflammatory pain.

Neuropathic pain is pain caused by damage or disease that affects the somatosensory system. Neuropathic pain is originated from spontaneous ectopic neuron discharge in the nervous system either in central or in peripheral. Due to the underlying etiologies are usually irreversible, most of neuropathic pain are chronic pain. Most people describe neuropathic pain as shooting, burning, tingling, lancinating, electric shock qualities, numbness, and persistent allodia. The nomenclature of neuropathic pain is based on the site of initiating nervous system with the etiology; for examples, central post-stroke pain, diabetes peripheral neuropathy, post-herpetic (or post-shingles) neuralgia, terminal cancer pain, phantom limb pain.

Mix-type pain is featured by the coexistence of both nociceptive and neuropathic pain. For example, muscle pain trigger central or peripheral neuron sensitization leading to chronic low back pain, migraine, and myofascial pain.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

Current therapy is directed to some or all of the pathogenetic components of inflammation. For example, corticosteroids have a broad spectrum of activities and NSAIDS are more specifically anti-prostaglandin and analgesic. All current therapies have relatively high rates of adverse effects and adverse effects are severe and serious.

There is a need for a composition and a method for treating inflammation, inflammatory-related disorders, and pain. The composition should be economic and easy to manufacture, and the method should be effective and have no significant side effects.

SUMMARY OF THE INVENTION

The present invention is directed to a pharmaceutical composition comprising a pharmaceutically acceptable carrier and an active compound of ω-(methylation)alkyl nitrile, or a pharmaceutically acceptable salt or solvate thereof. The compound is preferably at least 90% pure (w/w).

The present invention is also directed to a method for treating inflammation, inflammatory-related disorders, and pain. The method comprises the step of administering ω-(methylation)alkyl nitrile, or a pharmaceutically acceptable salt thereof to a subject in need thereof. The pharmaceutical composition comprising the active compound can be applied by any accepted mode of administration including topical, oral, and parenteral (such as intravenous, intramuscular, subcutaneous or rectal). Topical administration and oral administration are preferred.

DETAILED DESCRIPTION OF THE INVENTION

Definition

"Alkyl" refers to groups of from 1 to 12 carbon atoms, either straight chained or branched, preferably from 1 to 8 carbon atoms, and more preferably 1 to 6 carbon atoms.

"Aryl alkyl" refers to aryl-alkyl-groups preferably having from 1 to 6 carbon atoms in the alkyl moiety and from 6 to 10 carbon atoms in the aryl moiety. Such aryl alkyl groups are exemplified by benzyl, phenethyl and the like.

"Cycloalkyl" refers to cyclic alkyl groups of from 3 to 12 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$ (wherein X is $C_{1-4}$). "Solvates," as used herein, are addition complexes in which the compound is combined with an acceptable co-solvent in some fixed proportion. Co-solvents include, but are not limited to, ethyl acetate, lauryl lactate, myristyl lactate, cetyl lactate, isopropyl myristate, methanol, ethanol, 1-propanol, isopropanol, 1-butanol, isobutanol, tert-butanol, acetone, methyl ethyl ketone, acetonitrile, benzene, toluene, xylene(s), ethylene glycol, dichloromethane, 1,2-dichloroethane, N-methylformamide, N,N-dimethylformamide, N-methylacetamide, pyridine, dioxane, and diethyl ether.

ω-(Methylthio)alkylnitriles

The inventors have discovered that ω-(methylthio)alkylnitriles (Formula I) or a pharmaceutically acceptably salt or solvate thereof, are effective for treating inflammation, inflammatory-related disorders, and pain,

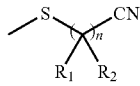

Formula I wherein $R_1$ and $R_2$ are independently H, straight-chain alkyl, branched alkyl, cycloalkyl, and arylalkyl, n=1-11.

Preferred ω-(methylthio)alkylnitriles useful for the present invention are compounds having $R_1$ and $R_2$ being H (Formula II), or a pharmaceutically acceptably salt or solvate thereof:

Formula II

Preferred compounds include 3-(methylthio)propionitrile (n=2, molecular weight=101.03), which is shown below.

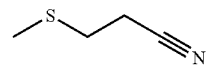

A series of ω-(methylthio)alkylnitriles can be prepared by alkylating sodium thiomethoxide with requisite ω-(halo) alkylnitriles. Alternatively, they can be prepared by alkylating sodium thiomethoxide with an ω-functionalized alkyl halide, followed by elaboration of the ω-functionality to a nitrile using established synthetic methodology.

Pharmaceutical Compositions

The present invention provides pharmaceutical compositions comprising one or more pharmaceutically acceptable carriers and an active compound ω-(methylthio)alkylnitrile, or a pharmaceutically acceptable salt, or solvate thereof. The active compound or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in a dosage form such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, lauryl lactate (for example, at about 0.1-10%, or about 0.2-5%, or about 0.5-5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the compound. Preferably lauryl lactate is purified to achieve ≥90%, preferably ≥95% purity; the high purity mitigates the presence of hydrolytic and oxidative agents. In addition, DMSO at 0.1-20%, or 0.5-10% (w/w) in the formulation provides suitable solubility of the active compound.

In another embodiment, diethylene glycol monoethyl ether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid resides in many cell membranes. When arachidonic acids are cleaved from the membranes, it can produce many of the known eicosinoids including prostaglandins and leucotrienes, which are known pro-inflammatory entities.

The active compounds are effective in inhibiting pro-inflammatory cytokine release (e.g., IL-1β, IL-6, TNFα, IL-4 and IFNγ) from human peripheral blood mononuclear cells in vitro. The active compound is anti-inflammatory when applied topically in the mouse ear swelling model, in which the inflammation is induced by arachidonic acid.

The present invention is directed to a method of treating inflammation and/or pain. The active compound, i.e., ω-(methylthio)alkylnitrile, preferably 3-(methylthio)propionitrile, can be used as is, or it can be administered in the form of a pharmaceutical composition that additionally contains a pharmaceutically acceptable carrier. The method comprises the steps of first identifying a subject suffering from inflammation and/or pain, and administering to the subject the active compound, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestations of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes nociceptive, neuropathic, and mix-type. The present invention reduces pain of varying severity, i.e. mild, moderate and severe pain; acute and chronic pain. The present invention is effective in treating joint pain, muscle pain, tendon pain, burn pain, and pain caused by inflammation such as rheumatoid arthritis.

In one embodiment, the present invention is useful in treating inflammation and/or pain associated in a musculoskeletal system or on the skin. The highly innervated, musculoskeletal and skin systems have a high capacity for demonstration of pain. In addition, the musculoskeletal system has a high capacity for tissue swelling, and the skin has a high capacity for redness, swelling, and heat. In musculoskeletal and skin systems, the degree of tissue damage is frequently magnified out of proportion to the resulting inflammatory response. In the skin for example, merely firm stroking will cause release of the cytokines, IL-1 and TNF.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. The skeletal or muscular diseases or conditions include musculoskeletal sprains, musculoskeletal strains, tendonopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epichondylitis (pitchers elbow) and trochanteric bursitis, temporomandibular joint syndrome, and fibromyalgia.

The present invention provides a method for treating inflammation and/or pain associated with inflammatory skin diseases such as dermatitis, psoriasis, and acne. The method comprises the steps of identifying a subject in need thereof, and administering to the subject the active compound, in an amount effective to treat inflammation and/or pain.

The present invention further provides a method for treating inflammatory skin diseases such as dermatitis, psoriasis, and acne (Acne vulgaris). The method comprises the steps of identifying a subject in need thereof, and administering to the subject the active compound, in an amount effective to reduce or eliminate the symptoms of the disease.

Skin is highly reactive to environmental stimuli and the epidermal component of keratinocytes is a very rich source of both arachidonic acid and pro-inflammatory cytokines of IL-1 and TNF. The skin dendritic cells, Langerhans cells, recognize and process antigens for further immune response of various lymphocytes and all of these cells are primarily regulated by cytokines through their specific cell surface receptors.

Dermatitis (also called eczema) is generic inflammation of the skin. Specific types of dermatitis include atopic, contact, nummular, and photo-induced.

Contact dermatitis is an inflammatory condition of the skin either of irritant exposure to the skin without specific adaptive immunologic pathogenesis or of allergic sensitization and subsequent exposure of the skin to the sensitizing allergen with specific adaptive immunologic pathogenesis. Both involve innate and acquired immune system response including arachidonic acid and cytokine components that initiate and propagate the disease through cell to cell messaging by eicosanoid and/or cytokine moieties produced by epidermal cells, macrophages, dendritic cells, neutrophils, eosinophils, and various T and B lymphocytes. Contact dermatitis may be either acute or chronic. The acute forms are pruritic with erythema, edema, and micro or macrovesiculation in the areas of skin contact by the initiating factor. The chronic forms are pruritic with milder erythema, scaling, lichenification, and possibly fissuring particularly on the hands.

Atopic dermatitis is a genetically determined disease that is part of the broader disease complex of atopy that includes asthma, hay fever, and atopic dermatitis. Many individuals with atopic dermatitis have various mutations of the filaggrin gene that codes for an important epidermal structural protein that when defective, results in abnormal barrier function of the epidermis. The altered barrier allows exposure to multiple environmental allergens that are first recognized by innate immune responses involving arachidonic acid and eicosanoids and recruitment of eosinophils, mast cells, and other inflammatory cells that initiate an acute responses of itch, erythema, and subsequent scratching and additionally activate the adaptive immune responses that involve inflammation by lymphocytes predominantly of a TH 2 derivation and activity. Atopic dermatitis is responsive to a number of cytokine inhibitors such as cyclosporine, and tacrolimus.

Current theory of the pathogenesis of psoriasis is that in individuals who are genetically susceptible a triggering event in the epidermis such as injury or super antigen contact initiates an response of the innate immune system with arachidonic acid and eicosanoid generation, recruitment and activity of neutrophils. Subsequent transformation of the response to that of a TH 1 adaptive immunity with cytokine activation and activity of specific T lymphocytes effect the pathological changes in the epidermis and dermis, which result in the typical psoriasis lesions of plaques that are erythematous, thickened, and scaly. Psoriasis is responsive to various immunomodulators including cyclosporine, methotrexate, and a host of specific biologicals that interfere with cytokine signaling.

Acne vulgaris, a progressively inflammatory disorder of the pilosebaceous follicular unit especially of the face and upper chest and back is a very common disease of both males and females after initiation of puberty, and in females even prior to adrenal gland maturity. Increased production of androgenic hormones by adrenal, ovarian, and testicular glands and by the pilosebaceous unit itself produce an increase in sebum and changes in its lipid composition, which combine with follicular epithelial cells to produce some degree of obstruction of the infra-infundibular portion of the pilosebaceous follicle resulting in the initial lesion of acne, the microcomedo. This consequent dilation of the pore and the changed composition of sebum at puberty facilitate colonization of the follicle by Propionibacterium acnes bacilli that produce enzymes to degrade the triglycerides in sebum to free fatty acids that leak through the follicle into the dermis and incite arachidonic acid pathways of eicosanoid production and subsequent initiation of inflammation. The bacilli also initiate chemokine production that attracts further inflammatory cells to the area and consequent cytokine production and action to continue and amplify inflammation. Thus initiation and propagation of progressive inflammation in the microcomedo produces the evolution to the several hallmark lesions of inflammatory acne, papule, pustule, nodule, and cyst. The present invention is useful to treat common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or acne medicamentosa.

Rosacea is a chronic condition characterized by facial erythema and sometimes pimples. Rosacea typically begins as redness on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop. There are 3 subtypes of rosacea that affect the skin: erythematotelangiectatic rosacea, papulopustular rosacea, and phymatous rosacea.

ω-(Methylthio)alkylnitriles, which are effective in inhibiting arachidonic acid induced inflammation and in inhibiting the release of pro-inflammatory cytokine, are effective to treat inflammation and/or pain associated with psoriasis, acne, rosacea, and dermatitis, particularly contact dermatitis, and atopic dermatitis.

ω-(Methylthio)alkylnitriles, which are effective in inhibiting arachidonic acid induced inflammation and in inhibiting the release of pro-inflammatory cytokine, are effective to treat inflammatory skin diseases such as dermatitis (atopic dermatitis), psoriasis, acne, and rosacea.

ω-(Methylthio)alkylnitriles are effective in treating atopic dermatitis and alleviating one or more symptoms selected from the group consisting of erythema, induration, lichenification, scaling, and oozing and crusting. Methanesulfonylalkylnitriles are effective in treating psoriasis and alleviating erythema, scaling, and/or thickness of the psoriasis lesions. Methanesulfonylalkylnitriles are effective in treating acne and alleviating acne lesions selected from the groups consisting of closed comedones, papules, pustules, nodules, and cysts.

ω-(Methylthio)alkylnitriles are effective in treating rosacea and alleviating one or more symptoms selected from the group consisting of erythema, telangiectasia, red domed papules and pustules, red gritty eyes, and burning and stinging sensations.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of active compounds delivered can vary; but are generally $1\times10^{-10}$-$1\times10^{-4}$ moles/liter, and preferably $1\times10^{-8}$-$1\times10^{-5}$ moles/liter.

In one embodiment, the composition is applied topically onto the affected area and rubbed into it. The composition is topically applied at least 1 or 2 times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally 1-50, and preferably 1-5 mg/kg/day.

In one embodiment, the pharmaceutical composition is administrated subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1

Preparing 3-(methylthio)propionitrile

3-Bromopropionitrile (203 mmol) was added dropwise to a chilled solution of sodium thiomethoxide (264 mmol) in water (80 mL). After stirring overnight at room temperature, the reaction mixture was transferred to a separatory funnel, and the lower aqueous phase was drained-off. The product which was in the upper phase was transferred to a tared vial containing sodium sulfate. Yield: 180 mmol; purity is >99% by gas chromatography.

Example 2

Anti-Inflammatory Activity of Active Compound by Topical Application in Mice 3-(Methylthio)propionitrile was prepared according to Example 1 and was used in this experiment.

The test compounds, indomethacin (positive control), and vehicle were evaluated for anti-inflammatory activity in a topical arachidonic acid-induced ear swelling model in mice.

Male ICR mice weighing 22±2 g were used and randomly divided; each group had 10 mice. Arachidonic Acid (0.5 mg in 20 μl of acetone:ethanol/1:1) was applied topically to the anterior and posterior surfaces of the right ear of each mice. Test substances and vehicle, as listed in Table 1 were similarly applied 30 min before and 15 min after arachidonic acid application. The thickness of the right ear and the left ear was measured and the difference calculated as an indication of the inflammation in the right ear. Ear swelling was measured by a Dyer model micrometer gauge at 60 and 90 minutes after arachidonic acid application as an index of inflammation. Percent inhibition was calculated according to the formula: Ic−It/Ic×100, where Ic and It refers to increase of ear thickness (mm) in control and treated mice, respectively. ANOVA and Dunnett's test were employed to ascertain significant difference between vehicle control and treated groups. Significance is set at P<0.05 level. The results measured at 90 minutes after arachidonic acid application are summarized in Table 1.

TABLE 1

| Test Substance | Conc mM | Dosage Mg/20 μL | n | % Inhibition | P Value |
|---|---|---|---|---|---|
| Vehicle - acetone:ethanol (1:1) | NA | NA | 10 | NA | |
| Indomethacin (Positive control) | 14 | 0.1 | 10 | 53 | <0.001 |
| 3-(methylthio)propionitrile | 375 | 1.0 | 10 | 43 | <0.001 |

The tested compound resulted in 43% inhibition in the ear swelling induced by arachidonic acid, relative to that in the vehicle-treated group. The differences between treated mice and vehicle-treated mice were determined to be statistically significant (p-value by t-test was <0.05).

Example 3

Gel Formulation 1

Table 2 exemplifies one gel formulation containing ω-(methylthio)alkylnitriles such as 3-(methylthio)propionitrile.

TABLE 2

| | 5% Gel | 1% Gel |
|---|---|---|
| Active compound | 5.0% | 1.0% |
| Dow Corning Elastomer Blend EL-8050 ID | 61.0% | 69.0% |
| Labrafac Lipophile WL 1349 | 8.0% | 8.0% |
| Octisalate | 5.0% | 5.0% |
| Lauryl Lactate | 1.1% | 3.2% |
| Dimethyl Sulfoxide (DMSO) | 8.9% | 1.8% |
| Dow Corning 556 Cosmetic Grade Fluid | 7.0% | 7.9% |
| Squalene | 2.0% | 2.0% |
| Sunflower Seed Oil | 2.0% | 2.0% |
| Dow Corning Aerogel VM-2270 | 0.1% | 0.0% |
| Total | 100.0% | 100.0% |

Example 4

Gel Formulation 2

Table 3 exemplifies another gel formulation containing ω-(methylthio)alkylnitriles such as 3-(methylthio)propionitrile.

TABLE 3

|  | 1-5% Gel |
| --- | --- |
| Active compound | 1.0-5.0% |
| Diethylene glycol monoethyl ether | 5.0% |
| Acrylates/C10-30 alkyl acrylate crosspolymer (CARBOPOL ® Ultrez 20 polymer) | 0.50% |
| Trolamine (tris(2-hydroxyethyl)amine) | 0.47% |
| Purified Water | 89.03-93.03% |
| Total | 100.0% |

Example 5

Inhibition of Cytokine Activities (Prophetic Example)

The active compounds ω-(methylthio)alkylnitriles such as 3-(methylthio)propionitrile are tested for their inhibitory effects on in vitro cytokine release from human peripheral blood mononuclear cells (PBMCs). Secretion of cytokines by PBMCs plays a significant role in the inflammatory response.

Each active compound is added to cultures of fresh human PBMCs at 162 µM (22 µg/mL) in duplicate. One hour later, PBMCs are stimulated to secrete cytokines using the mitogens lipopolysaccharide and concanavalin A (ConA). Lipopolysaccharide at 50 pg/mL is used to stimulate the release of interleukin IL-1β, IL-6 and tumor necrosis factor TNFα. ConA at 20 µg/mL is used to stimulate the release of IL-4 and ConA at 5 µg/mL is used to stimulate interferon IFNγ. The corticosteroid dexamethasone (100 nM) is used as a positive control. After 24 hours of incubation, the supernatants are assayed for the cytokines using the Luminex Bead kit. The percents inhibition of IL-1β, IL-6, TNFα, IL-4 and IFNγ by the active compounds and the positive compound are calculated. The results demonstrate that the active compound has an inhibitory effect on cytokines involved in the inflammatory process.

Example 6

Systemic Administration of Formulation (Prophetic Example)

This study is done to determine the systemic (plasma) exposure of test materials after administration by the oral and subcutaneous routes to rats.

The active compounds ω-(methylthio)alkylnitriles such as 3-(methylthio)propionitrile are tested are prepared in water for oral administration and in saline for subcutaneous administration. Rats are used in the study. Male rats are given a single dose at 50, 160 or 500 mg/kg by both oral and subcutaneous routes. Female rats (n=2) are dosed only at 500 mg/kg by both oral and subcutaneous routes. The blood is drawn from each rat at 0.25, 1, 2, 3, 4, 6, 12, 24, and 48 hours and measured for test material concentration by LC/MS/MS.

The average maximum plasma concentrations measured (Cmax) after oral dosing and after subcutaneous are determined. The above results demonstrate that significant bioavailability of test materials after both the oral and subcutaneous routes.

Example 7

Anti-Inflammatory Activity of Active Compounds in Mice by Oral Application (Prophetic Example)

The active compounds ω-(methylthio)alkylnitriles such as 3-(methylthio)propionitrile are suspended in a vehicle (1% Tween 80 in water) to 5-15 mg/mL. Test compounds, dexamethasone (positive control in vehicle), and vehicle are orally administered to mice and evaluated for anti-inflammatory activity in the topical arachidonic acid induced ear swelling model in mice.

Male ICR derived mice weighing 22±2 g are used in this experiment. 10-15 mice are used for each group (active compound, positive control, and vehicle). All animals are maintained in a controlled temperature (22-24° C.) and humidity (60%-70%) environment with 12-hour light/dark cycles for at least one week prior to use.

Arachidonic acid (0.5 mg in 20 µL acetone) is applied topically onto the anterior and posterior surfaces of the right ear of test animals to induce inflammation. Test compound in vehicle (10 mL/kg) and vehicle (10 mL/kg, 50-150 mg/kg) are orally administered by gavage 1 hour before arachidonic acid, whereas dexamethasone is orally administered by gavage 3 hour before arachidonic acid challenge. At 60 minutes and 90 minutes after arachidonic acid induction of ear edema, the thickness of the right ear and the left ear is measured and the difference calculated as an indication of the inflammation in the right ear. Significant activity is defined as a statistically significant inhibition (p-value determined by t-test was <0.05) in arachidonic acid induced ear swelling relative to the vehicle-treated group.

Example 8

Anti-Inflammatory and Analgesic Activity of Active Compounds in a Carrageenan Model (Prophetic Example)

The active compounds ω-(methylthio)alkylnitriles such as 3-(methylthio)propionitrile are prepared in the gel formulation according to Example 4.

Test materials in gel formulation (1-5%), indomethacin (positive control), and vehicle (gel formulation without active compound), are evaluated for anti-inflammatory and analgesic activity in the rat carrageenan-induced paw inflammation model.

Rats are used in the experiment. Carrageenan (0.1 mL of a 1% suspension) is injected subcutaneously into the left hind paw to induce inflammation. Test material (1-5%) or vehicle gel is applied to the paw topically at volumes of 0.05, 0.1 0.15 or 2.0 mL, 1.5, 2.5, and 3.5 hours following the carrageenan administration. Indomethacin is given orally at 5 mg/kg, 1 hour prior to carrageenan administration. The degree of inflammation (edema, or swelling) is determined using a plethysmograph to measure paw volume. Analgesia is determined by measuring paw withdrawal to a mechanical stimulus using von Frey filaments Inflammation and analgesia are measured 4 hours after carrageenan administration. Test materials are expected to have anti-inflammatory and/or analgesic properties as measured by a significant decrease in paw volume and/or a significant increase in mechanical pressure needed to elicit paw withdrawal, respectively, as compared to the vehicle control.

Example 9

Analgesic Activity of Active Compound in a Hot Plate Model (Prophetic Example)

The active compounds ω-(methylthio)alkylnitriles such as 3-(methylthio)propionitrile are prepared in the gel formulation according to Example 4.

Test materials: active compound in gel formulation (1-5%), morphine (positive control), and vehicle (gel formulation without active compound), are evaluated for analgesic activity in the rat hot plate model.

Rats are used in the experiment. Test material (1-5%) or vehicle gel is applied to the paw topically at volumes of 0.05, 0.1 0.15 or 2.0 mL. One hour later the rat is placed on a 55° C. hot plate, and the time to lick the paw is measured. The positive control, morphine, is given orally at 30 mg/kg, 1 hour prior to hot plate testing. Test materials are expected to have analgesic properties as measured by a significant increase in time to licking as compared to the vehicle control (t-test, $p<0.05$).

Example 10

Analgesic Activity of Active Compounds in CFA-Induced Thermal Hyperalgesia (Prophetic Example)

CFA (Complete Freund's Adjuvant) is known to induce inflammatory pain. (Walker, et al. JPET. 304: 56-62, 2003.)

Male Sprague-Dawley rats weighing 180±20 g are used. The animals, divided into groups of 8-10 each, receive a subplantar injection (0.1 ml) of CFA (0.1% solution) to the tested hindpaw at 24 hours prior to experimentation. Thermal hyperalgesia is tested by using the IITC Model-336G (IITC INC. USA) apparatus with a thermally regulated glass floors set at 30° C. Each rat is placed within a plastic box atop a glass floor. A light beam under the floor is aimed at the plantar surface of the right hind paw. The time is measured automatically when the paw is withdrawn away from the thermal stimulus. The intensity of the light is adjusted with average group baseline latency from 12 to 14 sec (pre-CFA) and a cut-off latency of 20 sec imposed. The latency to withdrawal is obtained for each rat and defined as the heat pain threshold. Twenty four hours after CFA injection, rats are pre-selected (with clear presence of thermal hyperalgesia) for experimentation only if the latency to withdrawal is less than 75% of baseline.

The active compounds ω-(methylthio)alkylnitriles such as 3-(methylthio)propionitrile are prepared in the gel formulation according to Example 4.

Active compounds in gel formulation (1-5%), active compounds in 1% Tween 80, morphine (positive control, p.o., 20 mg/kg), topical vehicle (gel formulation without an active compound), and oral vehicle (1% Tween 80 in water) are evaluated for analgesic activity in the formalin model.

Test substance or vehicle is either administered orally (20-60 mg/kg) or topically (1-5% gel formulation) to the plantar surface of the hind paw, at 60 minutes before the level of thermal hyperalgesia is again measured (post-treatment). Mean±SEM of thermal paw withdrawal time is calculated. Unpaired Student's t test is applied for comparison the values of post-treatment between test substance treated group and vehicle control group. Positive activity is considered at $P<0.05$.

Example 11

Analgesic Activity of Active Compounds in a Formalin Test (Prophetic Example)

Formalin test is a model of continuous pain resulting from formalin-induced tissue injury. The formalin model encompasses inflammatory, neurogenic, and central mechanism of nociception. The assay described below relates primarily to the late inflammatory algesic phase sensitive to both strong central analgesic as well as weaker analgesic/anti-inflammatory agents (Hunskaar, et al., J. Neuroscience Meth. 14: 69-76, 1985). The formalin test represents a suitable model for testing compounds for treating neuropathic pain (Benson, et al. Proceedings of Measuring Behavior, 2008, Eds. Spink, et al, 324-325).

The active compounds ω-(methylthio)alkylnitriles such as 3-(methylthio)propionitrile are prepared in the gel formulation according to Example 4. Active compounds in gel formulation (1-5%), active compounds in 1% Tween 80, morphine (positive control, p.o., 30 mg/kg), topical vehicle (gel formulation without an active compound), and oral vehicle (1% Tween 80 in water) are evaluated for analgesic activity in the formalin model.

Test substance is administered to groups of 8-10 CD-1 derived male mice weighing 23±3 g one hour before subplantar injection of formalin (0.02 ml, 2% solution). Test substance is either administered orally (20-60 mg/kg) or topically (1-5% gel formulation) to the plantar surface of the hind paw. Reduction of the induced hind paw licking time recorded during the following 10 to 30 minute period by 50% or more indicates analgesic activity. Positive activity is considered by a significant increase in time to licking in test compound as compared to the vehicle control (t-test, $p<0.05$).

Example 12

Analgesic Activity of Active Compounds in Chronic Constriction Injury Model (Prophetic Example)

Peripheral nerve lesions may generate a syndrome comprising, in addition to spontaneous pain, exaggerated responses to light touch (tactile allodynia). Chronic constriction injury model is a neuropathic pain model.

Male Sprague Dawley rats weighing 180±20 g are used. Under pentobarbital (50 mg/kg, 5 ml/kg, i.p.) anesthesia, the sciatic nerve is exposed at mid-thigh level. Four ligatures (4-0 chromic gut), about 1 mm apart, are loosely tied around the nerve. The animals are then housed individually in cages with soft bedding for 7 days before testing. Constriction of the sciatic nerve produces nerve injury and unilateral neuropathic pain.

On the day of experiments, the animals have no access to food overnight before testing. The rats are placed under inverted plexiglass cages on a wire mesh rack and allowed to acclimate for 20 to 30 minutes. Mechanic allodynia is evaluated by the Chaplan up/down method using von Frey filaments to the plantar surface of the left hind paw. See Chaplan, et al. J. Neuroscience Methods, 53: 55-63, 1994.

Rats are pre-selected for experimentation only if the pain threshold 7-14 days after nerve ligation (pre-treatment) is reduced by 10 grams of force relative to the response of the individual paw before nerve ligation (pre-ligation), namely, with clear presence of allodynia.

The active compounds ω-(methylthio)alkylnitriles such as 3-(methylthio)propionitrile are prepared in the gel formulation according to Example 4.

Active compounds in gel formulation (1-5%), active compounds in 1% Tween 80, morphine (positive control, p.o., 20 mg/kg), topical vehicle (gel formulation without an active compound), and oral vehicle (1% Tween 80 in water) are evaluated.

Test substance or vehicle is either administered orally (20-60 mg/kg) or topically (1-5% gel formulation) to the plantar surface of the left hind paw. The mechanical allodynia test is performed 30 min before (pre-treatment) and 1 and 3 hours after a single dose of test substance or vehicle (post treatment). Paw withdraw thresholds of control and tested compounds are measured.

Example 13

Treatment of Knee Pain (Prophetic Example)

Objectives: To investigate the efficacy of the active compound in a gel formulation in patients with mild to moderate knee pain associated with osteoarthritis following temporary cessation of standard NSAID therapy. The focus of this study is on the symptoms caused by painful arthritis. The clinical trial is utilizing osteoarthritis of the knee as a well-established paradigm for other musculoskeletal disorders.

Formulation: The gel formulation containing the active compound 3-(methylthio)propionitrile at 1% and 5% (Example 4) are used in this example. Placebo contains the same gel without the active compound.

Methodology: A randomized, double-blind, placebo controlled, parallel treatment multicenter clinical activity study.

Patients with painful osteoarthritis of the knee, controlled by a stable dose of standard NSAID therapy for at least 2 months, discontinue use of the NSAIDs for a 7 day washout period. Patients are then randomized in a 1:1:1 ratio (1% active gel, 5% active gel, placebo). A total of up to 150 patients are enrolled and treated for 7 days with follow-up at 8, 10, 14 and 21 days.

The active gel or placebo is applied to the affected knee 3 times a day for 7 days for a total of 21 treatments given every 4-6 hours while awake.

Patients are treated for 7 days and followed up for a further 14 days. NSAIDs may be restarted after the Day 10 visit.

Criteria for Evaluation:
Safety:
Adverse Events (AEs) throughout the study.
Physical examination at enrollment (-7 days, start of NSAID washout period), Baseline (Day 1, start of treatment), Day 10 and Day 21.
Vital signs at enrollment (-7 days, start of NSAID washout period), Baseline (Day 1, start of treatment) and Days 2, 4, 8, 10, 14 and 21.
Clinical laboratory measurements at Baseline (Day 1), Day 8 and Day 14.
Clinical Activity:
The primary clinical activity parameters are the measurement of pain at the site of application, as quantified by VAS and the Western Ontario and McMaster University (WOMAC) scale. The effect of treatment on swelling, tenderness and inflammation of the knee is recorded, also the time to reduction or eradication of pain after treatment is recorded.

Study Endpoints:
The primary clinical activity endpoint is:
Change from Baseline (Day 1) to Day 8 in WOMAC functional disability index:
Pain (Scale 0-20).
Stiffness (Scale 0-8).
Physical function (Scale 0-68).
The secondary clinical activity endpoints are:
Change from Baseline (Day 1) to Day 8 in VAS pain scale (1-100).
Within-day change in VAS pain scale on Day 2 and Day 3 as measured by change from daily Baseline (Pre-Treatment 1) to 30 minutes Post Treatment 2.
Change in investigator evaluation of swelling, tenderness and inflammation between Baseline (Day 1) and 30 minutes and 60 minutes after the first application on Day 1.
Change in investigator evaluation of swelling, tenderness and inflammation between Baseline (Day 1) and Day 8.
Time to reduction or eradication of pain subsequent to each topical application of active gel or placebo gel.
Use of rescue medication (APAP).

Example 14

Treatment of Atopic Dermatitis (Prophetic Example)

Objectives: To investigate the efficacy of the active compound in patients having atopic dermatitis.

Formulation: The active compounds ω-(methylthio)alkylnitriles such as 3-(methylthio)propionitrile are prepared in the gel formulation according to Example 4. Placebo contains the same gel without the active compound.

Methodology: This is a randomized, double-blind, placebo controlled, parallel treatment clinical activity study.

Male and female patients with mild to severe atopic dermatitis are enrolled after discontinuation of all treatments for atopic dermatitis for a period of 4 weeks before study initiation. Patients are randomized in a 1:1 ratio (active gel, placebo). A total of 300 patients are enrolled and treated.

The active gel or placebo is applied twice a day to affected areas of the body for 12 weeks. The treatment results are evaluated at 2 week intervals until week 12 and then at 4 weeks after discontinuation of the study medication application.

Criteria for Evaluation:
Safety:
Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).
Efficacy:
Efficacy is evaluated utilizing:
1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:
2. separate evaluation of a representative target atopic dermatitis area of involvement for erythema, induration, lichenification, scaling, and oozing and crusting with each parameter rated on a 0-4 scale with 0=none or clear, 1=almost clear, 2=mild disease involvement, 3=moderate disease involvement, and 4=severe disease involvement.

Statistical analyses of each of these efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 15

Treatment of Psoriasis (Prophetic Example)

Objectives: To investigate the efficacy of the active compound in patients having psoriasis vulgaris.

Formulation: The active compounds ω-(methylthio)alkylnitriles such as 3-(methylthio)propionitrile are prepared in the gel formulation according to Example 4. Placebo contains the same gel without the active compound.

Methodology: This is a randomized, double-blind, placebo controlled, parallel treatment clinical activity study.

Male and female patients with mild to severe psoriasis vulgaris are enrolled. Patients discontinue all treatments for psoriasis for a period of 4 weeks before study initiation. Patients are randomized in a 1:1 ratio (active gel, placebo). A total of 200 patients are enrolled and treated.

The active gel or placebo is applied twice a day to affected areas of the body for 12 weeks. The treatment results are evaluated at 2 week intervals until week 12 and then at 4 weeks after discontinuation of the study medication.

Criteria for Evaluation:
Safety:
Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).
Efficacy:
Efficacy is evaluated utilizing:
1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:
2. separate evaluation of a representative target psoriasis lesion for erythema, scaling, and thickness of each parameter rated on a 0-4 scale with 0=none or clear, 1=almost clear, 2=mild disease involvement, 3=moderate disease involvement, and 4=severe disease involvement.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 16

Treatment of Acne (Prophetic Example)

Objectives: To investigate the efficacy of the active compound in patients having acne vulgaris.

Formulation: The active compounds ω-(methylthio)alkylnitriles such as 3-(methylthio)propionitrile are prepared in the gel formulation according to Example 4. Placebo contains the same gel without the active compound.

Methodology: This is a randomized, double-blind, placebo controlled, parallel treatment clinical activity study.

Male and female patients with mild to severe acne vulgaris are enrolled. Patients discontinue all treatments for acne for a period of 4 weeks before initiation of the study. Patients are randomized in a 1:1 ratio (active gel, placebo). A total of 500 patients are enrolled and treated.

The active gel or placebo is applied to the affected area twice a day for 12 weeks. The treatment results are evaluated at 2 week intervals until week 12 and then at 4 weeks after discontinuation of the study medication.

Criteria for Evaluation:
Safety:
Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).
Efficacy:
Efficacy is evaluated utilizing:
1. an overall assessment of disease severity at study entry and at 2 week intervals until week 12 and subsequently at 4 weeks after discontinuation of the study medication. The investigator global assessment, IGA, is based upon a rating scale of 0 to 4 with 0=none or clear, 1=almost clear, 2=mild disease involvement, 3=moderate disease involvement, and 4=severe disease involvement, and:
2. separate counts of all types of acne lesions i.e. open and closed comedones, papules, pustules, nodules, and cysts.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

It is to be understood that the foregoing describes preferred embodiments of the present invention and that modifications may be made therein without departing from the scope of the present invention as set forth in the claims.

What is claimed is:

1. A pharmaceutical composition comprising a pharmaceutically acceptable carrier and 3-(methylthio)propionitrile, or a pharmaceutically acceptable salt thereof.

2. The pharmaceutical composition according to claim 1, wherein the compound has at least 90% (w/w) purity, and the composition is in a topical form of gels, creams, lotions, ointments, or patches.

3. The pharmaceutical composition according to claim 2, wherein the pharmaceutically acceptable carrier is an emollient selected from the group consisting of: lauryl lactate, diethylene glycol monoethyl ether, caprylic/capric triglyceride, octisalate, silicone fluid, squalene, and sunflower oil.

4. The pharmaceutical composition according to claim 2, wherein the pharmaceutically acceptable carrier is a permeation enhancer selected from the group consisting of lactate esters and diethylene glycol monoethyl ether.

5. The pharmaceutical composition according to claim 2, comprising diethylene glycol monoethyl ether, acrylates/C10-30 alkyl acrylate polymer, and tris(2-hydroxyethyl) amine.

6. The pharmaceutical composition according to claim 1, wherein the compound has at least 90% (w/w) purity, and the composition is in an oral form of tablets, capsules, or syrup.

7. The pharmaceutical composition according to claim 6, wherein the composition is in an oral form of tablets, capsules, or syrups.

* * * * *